(12) United States Patent
Palpu et al.

(10) Patent No.: US 7,399,491 B2
(45) Date of Patent: Jul. 15, 2008

(54) HEALTH PROMOTING FUNCTIONAL FOODS FORTIFIED WITH HERBS

(75) Inventors: Pushpangadan Palpu, Lucknow (IN); Ajay Kumar Singh Rawat, Lucknow (IN); Chandana Venkateswara Rao, Lucknow (IN); Sharad Kumar Srivastava, Lucknow (IN); Raghavan Govindarajan, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 342 days.

(21) Appl. No.: 11/024,007

(22) Filed: Dec. 28, 2004

(65) Prior Publication Data

US 2006/0141063 A1    Jun. 29, 2006

(51) Int. Cl.
*A61K 36/00* (2006.01)
(52) U.S. Cl. .................. 424/725; 424/769; 424/773
(58) Field of Classification Search ................ 424/725, 424/769
See application file for complete search history.

*Primary Examiner*—Christopher R Tate
*Assistant Examiner*—Randall Winston
(74) *Attorney, Agent, or Firm*—Ladas and Parry LLP

(57) ABSTRACT

The present invention provides a novel herbal composition, which promotes the proven pharmacological activities such as anti-oxidant, anti-stress and adaptogenic activities. Composition(s) comprises of plant juices or extracts together with the conventional recipients to form paste/jelly/jam/cake/cream puff/chocolate forms fortified with plants like *Mangifera indica, Evolvulus alsinoides, Withania somnifera* and *Asparagus racemosus Amaranthus hypochondriacus* which are used as functional foods.

33 Claims, No Drawings

HEALTH PROMOTING FUNCTIONAL FOODS FORTIFIED WITH HERBS

FIELD OF INVENTION

The present invention relates to health promoting functional foods fortified with herbs. The present invention also relates to a jam with a novel herbal composition. The present invention particularly relates to a novel herbal composition, which promotes proven pharmacological activities such as anti-oxidant, anti-stress and adaptogenic activities and comprises of plant juices or extracts together with the conventional recipients to form a paste/jelly/jam/cake/cream puff/chocolate forms fortified with these plants are added which are used as functional foods.

BACKGROUND AND PRIOR ART OF THE INVENTION

Human health depends to a large extent on three elements: spiritual harmony, physical activity and adequate nutrition. It has been observed over the last few decades that the stress of modern life, reduced physical activity and consumption of processed foods and chemicals preservatives, including over & unwanted use of modern drugs, are responsible for the decrease in the resistance to disease. Currently A "big-bang" is impacting the health food and pharmaceutical industries among others. This nutraceutical (nutrition plus pharmaceutical) explosion is derives from research publications providing scientific evidence to support hypothesis that phytochemicals in food and in isolated from provide health benefits to the consumer.

The vital aspect of nutraceutical is dietary disease preventive food component. Food industries have rather high demand for the products that meet the consumer's demand for a healthy life style. In this context functional food fortified with the plant ingredients plays an important role. These foods are not intended only to satisfy hunger and provide humans with necessary nutrients but also to prevent malnutrition related diseases and increases physical and mental well being of consumers.

The herbal revolution and its implementation to daily nutrient intake or function-fortified food/dietary supplements with desired therapeutic efficacy led the world populations' great interest in the same. This ultimately led to researchers to develop them in functional food and nutraceuticals and finally to develop marketable products. Functional foods are substances that provide health benefits beyond the normal nutritional values and nutrients added, which are not naturally occurring in that food are called as functional fortified food.

The plants are the major source among the Indian masses, since most important foods of mankind as these are not only nutritive but are also sometimes indispensable for the maintenance of health. There are some herbal food supplements available in the developed nations and a few in the developing ones.

OBJECTS OF THE INVENTION

The main objective of the present invention is to provide a synergistic novel health promoting functional food fortified with herbs having anti-stress and adaptogenic activity.

Another important objective is to provide a cost-effective health promoting functional food fortified with herbs.

SUMMARY OF THE INVENTION

The present invention provides a herbal composition useful as a nutrient, anti-stress and adaptogenic agent, the composition comprising plant juice or extracts of plants selected from the group consisting of *Mangifera indica, Evolvulus alsinoides, Withania somnifera, Asparagus racemosus* and *Amaranthus hypochondriacus*, together with excipients/additives.

In one embodiment of the invention, the extracts are obtained from powdered plant parts or lyophilized juice/extracts of plants.

In another embodiment of the invention, the plant extracts are obtained from plant parts selected from leaf, seeds, rhizome, tubers, aerial parts and any combination thereof.

In another embodiment of the invention, the plant part comprises *Mangifera indica* fruit.

In another embodiment of the invention, the plant part comprises *Withania somnifera* leaf or root in the form of powder.

In another embodiment of the invention, the plant part comprises *Asparagus racemosus* tuber in the form of powder.

In another embodiment of the invention, the plant part comprises *Amaranthus hypochondriacus* seed or leaves in the form of powder.

In another embodiment of the invention, the powder/juice or plant extracts are mixed in the ratio *Mangifera indica* 65-75 wt %, *Evolvulus alsinoides* 0.2-0.6 wt %, *Withania somnifera* 3.5-5 wt %, *Asparagus racemosus* 3.5-5 wt % and *Amaranthus hypochondriacus* 10-20 wt % along with conventional additives to form an oral dosage form.

In another embodiment of the invention, wherein the composition is used as a nutrient supplement and acts as a free radical scavenger.

In another embodiment of the invention, wherein the composition is in the form of paste/jelly/jam/cake/cream puff/chocolate.

In another embodiment of the invention, the composition exhibits antioxidant activity.

In another embodiment of the invention, the composition exhibits adaptogenic activity.

In another embodiment of the invention, the composition exhibits anti-stress activity.

In another embodiment of the invention, the composition exhibits enzymatic super oxide dismutase enhancing activity.

In another embodiment of the invention, the composition exhibits lipid peroxidation inhibition.

In another embodiment of the invention, the composition exhibits enzymatic enhancing catalase activity.

In another embodiment of the invention, the composition exhibits nonenzymic antioxidant activity.

In another embodiment of the invention, the composition exhibits shelf life of 1-2 years.

In another embodiment of the invention, the composition exhibits protein content in the range of 0.03-0.06 g per 10 g of composition.

In another embodiment of the invention, the composition exhibits essential amino acid content in the range of 28-33 mg per 10 g of composition.

In another embodiment of the invention, the composition exhibits leucine content in the range of 10-12 mg per 10 g of composition.

In another embodiment of the invention, the composition exhibits total carbohydrate and low fat content of about 0.01 g per 10 g of composition.

The present invention also relates to a method for the preparation of a method of preparing a herbal composition useful as a nutrient, anti-stress and adaptogenic agent, the composition comprising plant juice or extracts of plants selected from the group consisting of *Mangifera indica, Evolvulus alsinoides, Withania somnifera, Asparagus racemosus* and *Amaranthus hypochondriacus*, together with excipients/additives, the method comprising:

(a) selecting individual plant from the group consisting of leaves, fruits, seeds, root, rhizome, tubers, aerial parts or any combination thereof;

(b) crushing or powdering the plant material to juice or coarse powder;

(c) extracting the powdered dried plant material with an alcohol;

(d) preparing a syrup by heating 40-70% w/v sugar in water;

(e) mixing the plant extract of step (c) or juice of step (b) with the syrup obtained in step (d) to form a composition;

(f) concentrating the composition.

In one embodiment of the invention, the plant parts are used as such or are first dried in shade.

In another embodiment of the invention, step (c) is carried out with 40-50% aqueous ethanol and at a temperature in the range of 25-35° C. for a period of 3-7 days.

In another embodiment of the invention, step (f) is carried out at a temperature in the range of 80-120° C.

In one embodiment of the invention, the extracts are obtained from powdered plant parts or lyophilized juice/extracts of plants.

In another embodiment of the invention, the plant extracts are obtained from plant parts selected from leaf, seeds, rhizome, tubers, aerial parts and any combination thereof.

In another embodiment of the invention, the plant part comprises *Mangifera indica* fruit.

In another embodiment of the invention, the plant part comprises *Withania somnifera* leaf or root in the form of powder.

In another embodiment of the invention, the plant part comprises *Asparagus racemosus* tuber in the form of powder.

In another embodiment of the invention, the plant part comprises *Amaranthus hypochondriacus* seed or leaves in the form of powder.

In another embodiment of the invention, the powder/juice or plant extracts are mixed in the ratio *Mangifera indica* 65-75 wt %, *Evolvulus alsinoides* 0.2-0.6 wt %, *Withania somnifera* 3.5-5 wt %, *Asparagus racemosus* 3.5-5 wt % and *Amaranthus hypochondriacus* 10-20 wt % along with conventional additives to form an oral dosage form.

In another embodiment of the invention, the concentrated composition is converted to an oral dosage form selected from the group consisting of jam, jelly, paste, cream puff and chocolate.

DETAILED DESCRIPTION OF THE INVENTION

The present invention provides a herbal formulation useful in stress conditions as an anti-stress agent and adaptogenic activity. The herbal formulation comprising of *Evolvulus alsinoides* along with this, *Mangifera indica, Withania somnifera, Asparagus racemosus* and *Amaranthus hypochondriacus* are added to provide adaptogenic activity and relief in other symptoms. Out of the other plant parts *W. somnifera* showed 30-40% protection in stress induced gastric ulcers. Where as the formulation of the present invention showed highly significant (about 80%) results in stress induced gastric ulcers and therefore the formulation can be used as an adaptogenic and showed anti-stress activity. The plants used in the invention have the following properties.

*Mangifera indica* Linn Family: Anacardiaceae

Botanical description: A large, evergreen tree, 10-45 m tall, with a heavy, dome-shaped crown and a straight, stout bole. Bark thick, dark grey, flaking off when old. Leaves linear oblong or elliptic—lanceolate, 10-30 cm long and 2-9 cm wide, with an aromatic, resinous odour when crushed. Inflorescence a large panicle, containing up to 3000 flowers; flowers tiny, reddish-white or yellowish green with a pungent odour; staminate and hermaphrodite flowers borne in the same panicle. Fruit a large drupe, highly variable in form and size; fruit skin thick or thin, leathery, green, yellowish or red, often dotted with numerous glands; flesh (mesocarp) whitish-yellow, yellow or orange, firm, soft or juicy, slightly acidic to sweet, richly aromatic; seed solitary, ovoid-oblique, encased in a hard, compressed, fibrous endocarp (stone).

Phytochemistry: A new xanthane C-glycoside homo mangiferin isolated and characterized as 2C-beta D-glucopyranosyl-3-methoxy-1,6,7-trihydroxy xanthone (Chem. Pharm Bull 1970). Leucine, tyrosine and valine present in leaves, protocatechenic acid, catechin and mangiferin in born while alanine, glycine, gama aminobutyric acid, linic and shikimic acids found in both leaves and bark (Planta medica 1970). Beta sitosterol, catechin, epicatechin and leucocynidin found in seed coat (Curr. Sci. 1971). Isolation of mangiferin from bark and leaves; two new terpenoidal saponin indicoside A and B isolated and their structure determined (J. Nat. Prod 1993).

Pharmacology: Ripe mango fruit is a rich source of vitamins A and C, recommended as a laxative and diuretic and a restorative tonic, and useful for treating heat stroke. It is also thought to be useful for treating haemorrhage of the uterus, lungs and intestine. The unripe fruits are used for treating ophthalmia. The leaves are chewed to give tone to the gums. A cold aqueous extract of the tender leaves is taken internally to relieve diarrhoea in parts of southern orissa. The gum resin exuded from the cut bark is used in dressings for cracked feet and scabies, and is considered anti-syphilitic.

*Evolvulus alsinoides* Family: Convolvulaceae

Botanical Description: A perennial herb with a small woody and branched rootstock. Its branches are annual, numerous, more than 30 cm long, often prostrate, slender and wiry with long hairs. Leaves are small, entire, elliptic to oblong, obtuse, apiculate, base acute and densely hairy. Petiole is minute or nearly absent. Bracts are linear and persistent. Flowers mostly solitary in upper axils. Corolla blue rotate and broad funnel shaped, Calyx 4 is lobed, lanceolate and the tip acute. Peduncle is long and axillary. Capsule is globose and 4 valved. Seeds are 4 and glabrous.

Phytochemistry: The plant contains an alkaloid-shankhapushpine. Fresh plant contains volatile oil. It also contains a yellow neutral fat, an organic acid and saline substances. Three alkaloids—evolvine, betaine, and an unidentified compound have been isolated.

Pharmacology: The whole herb is used medicinally in the form of decoction with cumin and milk in fever, nervous debility, loss of memory and also in syphilis. Decoction of the drug, with Ocimum sanctum is administered in fevers accompanied by indigestion or diarrhoea. The root is used by the santals, for intermittent childhood fever. The leaves are made into cigarettes and smoked in chronic bronchitis and asthma. The plant is useful in internal haemorrhages. The oil promotes the growth of hair. Decoction was given in cases of malarial fever.

*Withania somnifera* Family: Solanaceae

Botanical description: An erect, evergreen, grayish tomentose shrub 0.3-2 m tall, with fairly long, stout, fleshy, whitish-brown roots. Leaves simple, alternate or subopposite. broadly ovate, glabrous, 5-12 cm long and 2.5-7 cm wide, apex subacute, base unequal, marginsentire, finely stellate-pubescent beneath; main nerves about 6 pairs; petioles 0.3-1.7 cm long.

Phytochemistry: Two new withnolides-5-dehydroxy withnolide R and with a somniferin A isolated and their structure established (Phytochemistry 1991). Isolation of two new withnolides sominone and sominolide and their characterization as 1alpha, 3beta, 27-trihydroxy 14 alpha, 15 alpha-epoxy 1-oxo-22(R) with a-2, 24 dienolide respectively (heterocycles 1992). Withasomidienone isolated and characterized as 27-hydroxy-3-ozo-22(R)- with a-1, 4, 24-trienolide (J. Nat. Prod 1991).

Pharmacology: The roots are considered alternative, germicidal, aphrodisiac and diuretic; they are used in Ayurveda to treat ulcers, fever, dyspnoea, cough, consumption, dropsy, rheumatism, toxicosis and memory loss. The powdered roots mixed with equal parts of honey and ghee is thought to be beneficial for impotence or seminial debility. The roots as well as the bruised leaves are also used externally to treat ulcers. painful swellings and scabies. The total alkaloids present in the roots produce relaxant and anti spasmodic effects. The fruits and seeds are diuretic. The leaves are considered anthelmintic and bitter, and their infusion is given to relieve fever.

*Asparagus racemosus* Family: Asparagaceae

Botanical description: A tall climbing, much-branched, spiny shrub with annual woody, white-grey or brown stems armed with strong, straight or recurved spines 0.5-1.3 cm long; rootstock short, tuberous, bearing numerous fusiform, succulent tuberous roots 30-100 cm long and 1-2 cm thick. Flowers white, fragrant, small, crowded in simple and branched racemes 5-15 cm long. Fruits globose, red when ripe, 3-lobed, 0.4-0.6 cm in diameter.

Phytochemistry: Quercetin-3-glucuronide isolated from leaves (Curr Sci 1969). Isolation of sitosterol, 4,6-dihydroxy-2-O-(2-hydroxy isobutyl)benzaldehyde and undeconyl cetanoate from roots (J. Indian. Chem Soc. 1991). A new polycyclic alkaloid asperagonine A—isolated from roots and its structure determined by X-ray analysis (Chem. Pharm. Bull 1994).

Pharmacology: In Ayurveda, the roots are considered alterative, stomachic, tonic, aphrodisiac and astringent. They are used to treat dysentery, tumours and inflammations. In unani the roots are used in the treatment of kidney and liver disorders. The fresh root juice mixed with honey, is given to relieve dyspepsia. The leaf paste is used in combination with warm water baths to relieve scabies among the kadars of Annamalai hills of Tamil Nadu.

*Amaranthus hypochondriacus* Family: Amaranthacea

Botanical description: *A. hypochondriacus* is a beautiful crop with red or green leaves. The plant is monoecious. An erect, branched, annual or perennial herb, varying in colour from green to purple, 30-60 cm tall with hard, strainght, paired axillary spines, Leaves long-petioled, oblong, ovate-elliptic or lanceolate, acute or obtuse, base cuneate, generally 1-6 cm long and 0.5-2.6 cm wide. Flowers minute, grayish-green, borne in dense axillary clusters or terminal spikes; bracts and bracteoles narrowly ovate-lanceolate. Fruit dehiscent, seeds oblong, black, compressed, shining.

Phytochemistry: The grain contains proteins, and is high in lysine, an essential amino acid in which cereal crops are low. Sulphur containing amino acids such as tryptophan, found to be deficient in pulses are present in amaranth seeds. The seeds are are also rich in calcium, iron and the b complex vitamins (Subramaniam and srinivasan 1952, Smith et al 1959).

Pharmacology: The plant is considered diuretic, emollient sudoritic and febrifuge, and is recommended for treating eruptive fevers, as a galactagogue and as a remedy for colic. A decoction of the plant is considered useful for improving digestion. The leaves are applied as a poultice to relieve bruises, abscesses, burns, wounds and inflammations; their infusion is used as a diuretic. The root is used to treat menorrhagia, gonorrhoea, eczema and inflammatory swelling. The powdered root is used as a cure for paronychia. The roots and leaves are boiled and given to children as a laxative. Among the Santhalis and Paharia in eastern Bihar, the root extract is given as a vermicide. In southern Orissa, however, an aqueous decoction of the root is given to check chronic diarrhoea. In Ayurvedic practice the root is used to treat uterine diseases. Recent studies have linked to reduction in cholesterol in laboratory animals.

The present invention provides a novel anti-stress herbal synergistic formulation useful for the treatment of acute adaptogenic and showing antioxidant properties. The formulation comprises 50% aqueous alcoholic extracts of plants comprising *Mangifera indica* 65-75 wt %, *Withania somnifera* 3.5-5 wt %, *Asparagus racemosus* 3.5-5 wt %. and *Amaranthus hypochondriacus* 10-20 wt %, *Evolvulus alsinoides* 0.2-0.6 wt % in an oral dosage form selected from the group consisting of paste/jelly/jam/cake cream puff/chocolate.

The novelty of the present investigation is (1) herbal formulation for the treatment of anti-stress (2) the herbal formulation for the treatment of adaptogenic activities.

The plants parts are selected from powdered plants or lyophilized juice/extracts of plants *Mangifera indica, Evolvulus alsinoides, Withania somnifera, Asparagus racemosus* and *Amaranthus hypochondriacus*. The herbal formulation used in the field of foods and pharmaceuticals as a nutrient comprises of plant juice or extracts together with the conventional excipients.

The plant extracts are obtained from plant parts selected from leaf, seeds, rhizome, tubers and aerial parts. The plant parts preferably used are *Mangifera indica* fruit; powder obtained from *Withania somnifera* leaves or roots; powder obtained from *Asparagus racemosus* tubers; and powder obtained from *Amaranthus hypochondriacus* seed or leaves.

The formulation is useful as a nutrient supplement and acts as a free radical scavenger.

The extracts used are alcoholic extracts wherein the alcohol used is aqueous ethanol (40-50%).

The method of preparation comprises:

a. selecting individual part of plants from a group comprising leaves, fruits, seeds root, rhizome, tubers and aerial parts of equal proportion;

b. using fresh or shade dried plant materials, c. crushing/powdering the plant material to Juice/coarse powder, d. extracting powdered dried plant material with (40-50% aqueous ethanol) at 25-35° C., e. preparing a syrup by heating 40-70% w/v sugar in water, f. mixing plant extract or juice obtained in step (e) of *Mangifera indica, Evolvulus alsinoides, Withania somnifera, Asparagus racemosus Amaranthus hypochondriacus* in syrup;

g. concentrating the composition at high temperature (80-120° C.) to form a paste/jelly/jam/cake/cream puff/chocolate.

The formulation exhibits potent antioxidant activity, potent adaptogenic activity, potent anti-stress activity, potent enzymatic super oxide dismutase enhancing activity, potent lipid peroxidation inhibition, potent enzymatic enhancing catalase activity, and potent nonenzymic antioxidant activity.

It was also observed that the formulation showed an enhanced protein content (0.03-0.06 g/10 g), an enhanced essential amino acid content 28-33 mg/10 g), an enhanced leucine content 10-12 mg/10 g) and an enhanced total carbohydrate and low fat content (0.01 g/10 g).

The extracts on basis of one or more bioactive components are combined in one convenient but tasty formula of fruits in the form of jam or jellies. The herbal formulation is helpful in defending the human body against effects of stressful environment and provides vitality and energy.

Each formulation has been described below in detail giving the formula of the ingredients along with the method of preparation.

The first step in the preparation of these formulations involves a process for making, the plant material suitable for formulating into a solid/semi solid form. The specified portion of the plant is collected and dried under shade at room temperature (25-35° C.) for 72 hours or until the material gets dried. The material is then powdered into a fine powder. A specified amount of the powdered material is then extracted exhaustively with 50% aqueous alcohol at room temperature (25-35° C.). Extraction was carried out in a closed container immersing specified amount of the plant material in specified solvent (1:8 or 1:15 ratio) for 4-7 days. At the end of this stage, solvent is decanted and filtered if necessary to make it free from plant debris. The solvent is then concentrated by evaporating under vacuum at less than 40-60° C. The concentrate is then freeze dried to obtain final product in powder form.

Following example are given by illustration and therefore should not be construed to limit the scope of the present invention.

EXAMPLE 1

| Formulation (F1) | |
|---|---|
| *Mangifera indica* | 65 wt. % |
| *Evolvulus alsinoides* | 0.4 wt. % |
| *Withania somnifera* | 3 wt. % |
| *Asparagus racemosus* | 4 wt. % |
| *Amaranthus hypochondriacus* | 14 wt. % |
| Syrup | 66.7 w/w % |
| Distilled water | q.s. to make 100% |

*Mangifera indica, Evolvulus alsinoides, Withania somnifera, Asparagus racemosus* and *Amaranthus hypochondriacus* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. 15 g of starch is mixed with water and heated to form a paste. The weighed quantities of the plant extracts are then blended with excipients sufficiently to make 100 g. The ingredients are then mixed properly with the starch paste to form a mass. The formulation is useful for the adaptogenic, stress and nutrient.

EXAMPLE 2

| Formulation (F2) | |
|---|---|
| *Mangifera indica* | 65 wt. % |
| *Evolvulus alsinoides* | 0.5 wt. % |
| *Withania somnifera* | 6 wt. % |
| *Asparagus racemosus* | 6 wt. % |
| *Amaranthus hypochondriacus* | 15 wt. % |
| Syrup | 66.7 w/w % |
| Distilled water | q.s. to make 100% |

*Mangifera indica, Evolvulus alsinoides, Withania somnifera, Asparagus racemosus* and *Amaranthus hypochondriacus* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Details are as given in example 1

Procedures for Adaptogenic Activity

The Following Parameter are Used to Assess the Intensity of Stress-induced Effect Gastric Ulceration: The stomach was removed and split open along the greater curvature. The number of discrete ulcers was noted by the help of a magnifying glass. The severity of the ulcers was scored after histological conformation as, 0=no ulcers, 1=changes limited to superficial layers of the mucosa with no congestion, 2=half the mucosal thickness showing necrotic changes and congestion, 3=more than two-thirds of mucosal thickness showing necrotic changes and congestion and 4=complete destruction of the mucosa with marked hemorrhage. Thereafter, the pooled ulcer severity score was calculated. The blood was collected and serum was separated and enzyme like alkaline phosphatase, acid phosphatase, glutamic pyruvic transaminase, lipid peroxidation, superoxide dismutase and catalase are estimated by span diagnostic kit method.

TABLE 1

Effect of formulation on chronic stress-induced gastric ulceration in rats

| S. No | Treatment groups (100 mg/kg, p.o.) | Ulcer incidence (%) | Number of ulcers | Severity of ulcers |
|---|---|---|---|---|
| 1 | Vehicle + stress | 100 | 19.5 ± 2.5 | 32.8 ± 6.2 |
| 2 | F1 | 50 | 10.2 ± 2.1$^a$ | 16.3 ± 2.5$^b$ |
| 3 | F2 | 40 | 8.2 ± 2.0$^b$ | 12.5 ± 2.6$^b$ |
| 4. | Commercially available marketed sample | 83 | 16.8 ± 2.9 | 26.8 ± 5.8 |

Values are mean ± S.E.M.
P: $^a$<0.01 and $^b$<0.001 compared to respective control group.

NOTE:

No mortality was found in any of the treated group.

No gross abnormality in behavior was observed in the animal exposed with herbal preparation.

Formulation F1 contains extracts of *Mangifera indica* (65 wt. %), *Evolvulus alsinoides* (0.4 wt. %), *Withania somnifera* (3 wt. %), *Asparagus racemosus* (4 wt. %) and *Amaranthus hypochondriacus* (14 wt. %).

Formulation F2 contains extracts of *Mangifera indica* (65 wt. %), *Evolvulus alsinoides* (0.5 wt. %), *Withania somnifera* (6 wt %), *Asparagus racemosus* (6 wt %) and *Amaranthus hypochondriacus* (15 wt %).

As indicated in Table 1, Formulation F2 acts as an anti-ulcer agent in stress as indicated in reduction of ulcer index from 100% to 40%, number of ulcers from 19.5 to 8.2 and also decrease in severity of ulcers from 32.8 to 12.5.

Commercially available marketed sample did not showed any protective effect in the ulcerated stomachs. This effect was observed only with formulation F1 and F2. Of the two, formulation F2 is more significant.

TABLE 2

Effect of formulation on chronic stress-induced changes in adrenal gland, lipid peroxidaation, superoxide dismutase and catalase in rats

| S. No | Treatment groups (mg/kg, p.o.) | Adrenal Gland Wt (mg/100 g) | Lipid peroxidation | Catalase |
|---|---|---|---|---|
| 1 | Vehicle | 22.8 ± 3.9 | 0.45 ± 0.02 | 33.9 ± 2.4 |
| 2 | Vehicle + stress | 39.7 ± 5.2 | 0.71 ± 0.04$^x$ | 19.5 ± 1.9$^x$ |
| 3 | F1 | 25.8 ± 4.2$^b$ | 0.41 ± 0.02$^c$ | 26.7 ± 3.1$^a$ |
| 4 | F2 | 31.4 ± 2.9$^a$ | 0.28 ± 0.02$^c$ | 29.3 ± 2.7$^a$ |

Values are mean ± S.E.M.
P: $^x$<0.001 compared to respective vehicle (control) group.
P: $^a$<0.05, $^b$<0.01 and $^c$<0.001 compared to respective vehicle control group.

NOTE:

No mortality was found in any of the treated group.

No gross abnormality in behavior was observed in the animal exposed with herbal preparation.

Formulation F1 contains extracts of *Mangifera indica* (65 wt. %), *Evolvulus alsinoides* (0.4 wt. %), *Withania somnifera* (3 wt. %), *Asparagus racemosus* (4 wt. %) and *Amaranthus hypochondriacus* (14 wt. %).

Formulation F2 contains extracts of *Mangifera indica* (65 wt. %), *Evolvulus alsinoides* (0.5 wt. %), *Withania somnifera* (6 wt %), *Asparagus racemosus* (6 wt %) and *Amaranthus hypochondriacus* (15 wt %).

Adrenal gland weight was increased in chronic stress with the formulation F1 and F2. The lipid peroxidation was significantly increased in vehicle+stress group compared to the vehicle group, when we treated with the developed formulations there is a significant decrease in the increased levels and attained to near to normal values. The antioxidant enzyme catalase was concomitantly increased from 19.5 to 29.3 and this showed a positive effect compared to the vehicle plus stress group.

TABLE 3

Effect of formulations on biochemical changes in rats.

| S. No | Treatment | Alkaline phosphatase | Acid phosphatase | Glutamic pyruvic transaminase |
|---|---|---|---|---|
| 1 | Control | 8.12 ± 0.25 | 3.98 ± 0.5 | 63.9 ± 0.41 |
| 2 | F1 | 7.98 ± 0.19 | 3.65 ± 0.4 | 65.3 ± 0.39 |
| 3 | F2 | 8.23 ± 0.26 | 3.75 ± 0.5 | 66.5 ± 0.42 |

Values are mean ± S.E.M.

NOTE:

No mortality was found in any of the treated group.

No gross abnormality in behavior was observed in the animal exposed with herbal preparation.

Formulation F1 contains extracts of *Mangifera indica* (65 wt. %), *Evolvulus alsinoides* (0.4 wt. %), *Withania somnifera* (3 wt. %), *Asparagus racemosus* (4 wt. %) and *Amaranthus hypochondriacus* (14 wt. %).

Formulation F2 contains extracts of *Mangifera indica* (65 wt. %). *Evolvulus alsinoides* (0.5 wt. %), *Withania somnifera* (6 wt %), *Asparagus racemosus* (6 wt %) and *Amaranthus hypochondriacus* (15 wt %).

There is no change in the levels of the enzymes viz. alkaline phosphatase, acid phosphatase and glutamic pyruvic transaminase.

Quality Control of Jam

| Paramaters | Values/10 g jam |
|---|---|
| Calories | 33.12 Kcal |
| PH | 3.56 |
| Dry matter | 66% |
| Reduced Sugar | 51% |
| Total sugar | 6.32 g |
| Total Fibre | 0.35 g |
| Sodium | 4.32 mg |
| Potassium | 3.26 mg |
| Calcium | 1.69 mg |
| Proteins | 0.05 g |
| Amino acids | |
| Alanine | 5.08 |
| Valine | 1.28 |
| Leucine | 10.41 |
| Proline | 6.26 |
| Lysine | 6.23 |
| Total fat | 0.01 g |

Shelf Life

Hydroxymethylfurfural (HMF) is a recognized indicator of quality deterioration, as a result of excessive heating or storage in a wide range of foods containing carbohydrates. Its content is practically zero in fresh, untreated fruit juice and HMF formation is judged to be the most useful method for assessing the effectiveness of heat treatment in destroying spoilage organisms in jams and fruit products.

HMF content immediately after preparation 1.34 mg HMF/100 g of Jam and after 1 year, it is 1.64 mg HMF/100 g Jam at room temperature.

We claim:

1. An herbal composition useful as nutrient, anti-stress and adaptogenic agent, the composition comprising plant powders, juices, extracts, or mixtures thereof obtained from a combination of the plants *Mangifera indica, Evolvulus alsinoides, Withania somnifera, Asparagus racemosus* and *Amaranthus hypochondriacus* and one or more excipients, additives or a mixture thereof, wherein the powders, juices, extracts, or mixtures thereof are mixed in the ratio of 65-75 wt % *Mangifera indica,* 0.2-0.6 wt % of *Evolvulus alsinoides,* 3.5-5 wt % of *Withania somnifera,* 3.5-5 wt % of *Asparagus racemosus* and 10-20 wt % of *Amaranthus hypochondriacus* in combination with the one or more excipients, additives or mixture thereof.

2. The composition as claimed in claim 1 wherein the extracts are obtained from powdered plant parts, or lyophilized juice or extracts of the plants.

3. The composition as claimed in claim 1 wherein the plant extracts are obtained from plant parts selected from leaf, seeds, rhizome, tubers, aerial parts and any combination thereof.

4. The composition as claimed in claim 1 wherein the plant part comprises *Mangifera indica* fruit.

5. The composition as claimed in claim 1 wherein the plant part comprises *Withania somnifera* leaf or root in the form of a powder.

6. The composition as claimed in claim 1 wherein the plant part comprises *Asparagus racemosus* tuber in the form of a powder.

7. The composition as claimed in claim 1 wherein the plant part comprises *Amaranthus hypochondriacus* seed or leaves in the form of a powder.

8. The composition as claimed in claim 1 wherein the composition is used as a nutrient supplement and acts as a free radical scavenger.

9. The composition as claimed in claim 1 wherein the composition is in the form of a paste, jelly, jam, cake, cream puff, or chocolate.

10. The composition as claimed in claim 1 wherein the composition exhibits antioxidant activity.

11. The composition as claimed in claim 1 wherein the composition exhibits adaptogenic activity.

12. The composition as claimed in claim 1 wherein the composition exhibits anti-stress activity.

13. The composition as claimed in claim 1 wherein the composition exhibits enzymatic super oxide dismutase enhancing activity.

14. The composition as claimed in claim 1 wherein the composition exhibits lipid peroxidation inhibition.

15. The composition as claimed in claim 1 wherein the composition exhibits enzymatic enhancing catalase activity.

16. The composition as claimed in claim 1 wherein the composition exhibits nonenzymic antioxidant activity.

17. The composition as claimed in claim 1 wherein the composition has a shelf life of 1-2 years.

18. The composition as claimed in claim 1 wherein the composition has a protein content in the range of 0.03-0.06 g per 10 g of composition.

19. The composition as claimed in claim 1 wherein the composition has an essential amino acid content in the range of 28-33 mg per 10 g of composition.

20. The composition as claimed in claim 1 wherein the composition has a leucine content in the range of 10-12 mg per 10 g of composition.

21. The composition as claimed in claim 1 wherein the composition has a total carbohydrate and low fat content of about 0.01 g per 10 g of composition.

22. A method for preparing an herbal composition useful as a nutrient, anti-stress and adaptogenic agent, the composition comprising plant powders, juices, extracts or a mixture thereof, whereby the herbal composition is obtained from a combination of the plants *Mangifera indica, Evolvulus alsinoides, Withania somnifera, Asparagus racemosus* and *Amaranthus hypochondriacus* and one or more excipients, additives or a mixture thereof: the method comprising the steps of: (a) for each of the plants selecting individual plant parts from the group consisting of leaves, fruits, seeds, root, rhizome, tubers, aerial parts or any combination thereof; (b) crushing or powdering the plant material to juice or coarse powder; (c) extracting the powdered dried plant material with an alcohol; (d) preparing a syrup by heating 40-70% w/v sugar in water; (e) mixing the plant extract of step (c) or juice of step (b) with the syrup obtained in step (d) to form a composition; and (f) concentrating the composition, wherein the plant powders, juices, extracts and/or mixtures thereof are mixed in the ratio *Mangifera indica* 65-75 wt %, *Evolvulus alsinoides* 0.2-0.6 wt %, *Withania somnifera* 3.5-5 wt %, *Asparagus racemosus* 3.5-5 wt % and *Amaranthus hypochondriacus* 10-20 wt % in combination with the one or more excipients, additives or mixtures thereof to form an oral dosage form.

23. A method as claimed in claim 22 wherein the plant parts are used as such or are first dried in shade.

24. A method as claimed in claim 22 wherein step (c) is carried out with 40-50% aqueous ethanol and at a temperature in the range of 25-35° C. for a period of 3-7 days.

25. A method as claimed in claim 22 wherein step (f) is carried out at a temperature in the range of 80-120° C.

26. A method as claimed in claim 22 wherein the extracts are obtained from powdered plant parts or lyophilized juice/extracts of plants.

27. A method as claimed in claim 22 wherein the plant extracts are obtained from plant parts selected from leaf, seeds, rhizome, tubers, aerial parts and any combination thereof.

28. A method as claimed in claim 22 wherein the *Mangifera indica* plant part is the fruit. *Withania somnifera* plant part is the leaf or root in the form of powder.

29. A method as claimed in claim 22 wherein the *Withania somnifera* plant part is the leaf or root in the form of powder.

30. A method as claimed in claim 22 wherein the *Asparagus racemosus* plant part is the tuber in the form of powder.

31. A method as claimed in claim 22 wherein the *Amaranthus hypochondriacus* plant part is the seed or leaves in the form of powder.

32. A method as claimed in claim 22 wherein the concentrated composition is converted to an oral dosage form selected from the group consisting of jam, jelly, paste, cream puff and chocolate.

33. The composition of claim 1 in an oral dosage form.

* * * * *